United States Patent [19]

Fehr

[11] Patent Number: 4,701,278

[45] Date of Patent: Oct. 20, 1987

[54] UTILIZATION OF A CYCLOALIPHATIC CARBINOL AS PERFUMING INGREDIENT

[75] Inventor: Charles Fehr, Versoix, Switzerland

[73] Assignee: Firmenich SA, Geneva, Switzerland

[21] Appl. No.: 792,999

[22] Filed: Oct. 30, 1985

[30] Foreign Application Priority Data

Nov. 6, 1984 [CH] Switzerland .......................... 5308/84

[51] Int. Cl.[4] .......................... A61K 7/46; C11D 3/50

[52] U.S. Cl. .................................... 252/132; 252/8.6; 252/174.11; 252/DIG. 13; 424/65; 514/844

[58] Field of Search .............. 252/174.11, 522 R, 132, 252/8.6

[56] References Cited

U.S. PATENT DOCUMENTS 4,006,218 2/1977 Sipos .................................... 424/54

FOREIGN PATENT DOCUMENTS 58-96002 6/1983 Japan .

OTHER PUBLICATIONS

Okazawa, N. E. et al., "Solution Carbocation Stabilities . . . Hydride Ion", *Can. J. Chem.* 60, pp. 2180–2193, Sep. 1, 1982.

*Primary Examiner*—Dennis L. Albrecht
*Attorney, Agent, or Firm*—Pennie & Edmonds

[57] ABSTRACT

4-Cyclohexyl-2-methyl-2-butanol of formula

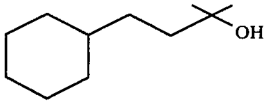

possesses useful fragrance properties and consequently it can be used advantageously for the preparation of perfumes and perfumed consumable materials. It develops especially flowery type odor notes.

4 Claims, No Drawings

UTILIZATION OF A CYCLOALIPHATIC CARBINOL AS PERFUMING INGREDIENT

BRIEF SUMMARY OF THE INVENTION

The present invention relates to a method to confer, enhance or modify the fragrance properties of perfumes and consumable materials, which method comprises the step of adding thereto a fragrance effective amount of 4-cyclohexyl-2-methyl-2-butanol, a cycloaliphatic carbinol of formula

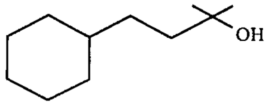

This invention relates also to a perfume composition or a consumable material containing, as fragrance active ingredient, 4-cyclohexyl-2-methyl-2-butanol.

THE INVENTION

I have discovered that 4-cyclohexyl-2-methyl-2-butanol possesses useful fragrance properties and, consequently, it can be advantageously used in a variety of applications, both in fine and in technical perfumery. Its ordorous properties are such that it can be conveniently utilized to develop flowery type notes reminiscent of those developed by lily-of-the-valley and of coriander. Its ordor character is particularly elegant and it possesses strong body so that it can be used to enrich various types of perfume compositions by conferring thereto elegance and naturalness.

Its scent is somehow reminiscent of linalol, tetrahydrolinalol, dimetol or 4-isopropyl-cyclohexylmethanol (MAYOL, registered trademark of Firmenich SA) and in many specific applications it can be used as a coingredient in a mixture with these compounds in order to complete the fragrance developed by them.

The proportions in which the carbinol of the invention can be used in order to achieve the desired effects vary within a wide range of values. Those skilled in the art will appreciate that these values depend on the specific effect it is desired to achieve and on the nature of the coingredients present in a given composition or on the nature of the products it is desired to perfume. Thus, concentrations of the order of 0.1–0.5% by weight, based on the total weight of the perfumed end-material, can already produce marked effects in applications such as the perfuming of soaps, detergents or fabric softeners. When the cycloaliphatic carbinol of the invention is used as an ingredient in concentrated perfume compositions, these proportions can reach much higher value, for example, they can be of the order of 2 to 5% and being as high as 20 or 30% of the weight of the total composition.

As indicated above, 4-cyclohexyl-2-methyl-2-butanol can find an advantageous utilization as a fragrance ingredient in functional products. It can be used, for instance, to perfume soaps, cationic, anionic, zwitterionic and nonionic solid and liquid detergents, fabric softeners, air-fresheners, body and room deodorizers, polymeric materials, household products, waxes, as well as cosmetics and shampoos. Of course, the cycloaliphatic carbinol of the invention can be used as a sole ingredient or preferably, in admixture with other current perfume coingredients (as an example of suitable natural and synthetic coingredients, one may cite the compounds mentioned in the European patent application published under No. 0096243, disclosure of which is enclosed herein by reference).

4-Cyclohexyl-2-methyl-2-butanol is a known chemical entity, namely described by N. E. Okazawa et al. [Can. J. Chem., 60, 2180–93 (1982)] (see the manufacturing process described by these authors). Its fragrance properties, however, have not been described in the art and its utilization has remained so far unrecognized.

The compound used according to the present invention possessed the following analytical characters.

Ir (liquid film): 3350, 2900, 1440, 1370, 1140 and 900 $cm^{-1}$;

MS: m/e: 59(100), 55(23), 81(19),41(18),95, 67 and 43(12).

B.p.: 63°–64°/6.65 Pa.

The invention is illustrated in a more detailed manner by the following examples.

EXAMPLE 1

A base perfume composition has been prepared by mixing the following ingredients (parts by weight):

| | |
|---|---|
| Benzyl salicylate | 160 |
| Phenethylol | 120 |
| Isononyl acetate | 80 |
| Benzyl acetate | 80 |
| Heliotropin | 40 |
| Hydroxycitronellal | 40 |
| Geranyl acetate | 40 |
| Citronellol | 40 |
| Undecylenic aldehyde 10%* | 40 |
| Musk DTI(1) (2) | 30 |
| Hexylcinnamaldehyde | 30 |
| Isomethylionone | 30 |
| Linalol | 20 |
| alpha-Damascone 10%*(1) | 20 |
| Styrallyl acetate | 20 |
| gamma-Decalactone | 20 |
| Decylaldehyde 10%* | 20 |
| 3-cis-Hexenyl salicylate 10%*(1) | 20 |
| Lilial (reg. tm)(3) | 20 |
| Hedione (reg. tm)(1) | 20 |
| beta-Damascenone 1%*(1) | 10 |
| | 900 |

*in diethyl phthalate
(1)origin: Firmenich SA, Geneva
(2)(6-tert-butyl-1,1-dimethylindane-4-yl)-1-ethanone
(3)alpha-methyl-p-tert-butyl hydroxycinnamaldehyde; origin: L. Givaudan, Vernier (Switzerland)

By adding to the flowery type base composition described above 100 g of 4-cyclohexyl-2-methyl-2-butanol, a novel composition resulted with an elegant and more rounded olfactive character.

EXAMPLE 2

| | Composition | Composition with sodium perborate |
|---|---|---|
| Sodium linear alkyl-benzene-sulphonate (chain length: $C_{11-5}$) | 8.0 | 6.4 |
| Ethoxylated tallow alcohol (14EO) | 2.9 | 2.3 |
| Sodium soap (chain length: $C_{12-16}$13–26%; $C_{18-22}$74–87%) | 3.5 | 2.8 |
| Sodium triphosphate | 43.8 | 35.0 |
| Sodium silicate | 7.5 | 6.0 |
| Magnesium silicate | 1.9 | 1.5 |
| Carboxymethylcellulose | 1.2 | 1.0 |
| Sodium EDTA | 0.2 | 0.2 |
| Sodium sulphate | 21.2 | 17.0 |
| Water | 9.8 | 7.8 |

-continued

| | Com-position | Composition with sodium perborate |
|---|---|---|
| Sodium perborate | — | 20.0 |
| | 100.0 | 100.0 |

By adding to a sample of each of the above detergent bases 1% by weight of 4-cyclohexyl-2-methyl-2-butanol, two novel compositions resulted whose flowerey scent was reminiscent of lily-of-the-valley.

What I claim is:

1. A method to enhance or modify flowery type perfume notes, reminiscent of those developed by lily-of-the-valley and coriander, of perfumes and consumable materials, which comprises adding thereto a fragrance effective amount of 4-cyclohexyl-2-methyl-2-butanol in admixture with other perfume coingredients.

2. A method according to claim 1 wherein the 4-cyclohexyl-2-methyl-2-butanol is in admixture with linalol, tetrahydrolinalol, dimetol or 4-isopropylcyclohexyl methanol.

3. A method according to claim 1 wherein the consumable material is a soap, a cationic, anionic, zwitterionic or non-ionic solid and liquid detergent, a fabric softener, and air freshener, a body and room deodorizer, a polymeric material, a wax, a cosmetic or a shampoo.

4. A product made by the process of claim 1 wherein the consumable material is a soap or a solid or liquid detergent.

* * * * *